United States Patent [19]

Uda et al.

[11] Patent Number: 4,823,368
[45] Date of Patent: Apr. 18, 1989

[54] OPEN COUNTER FOR LOW ENERGY ELECTRON DETECTION WITH SUPPRESSED BACKGROUND NOISE

[75] Inventors: Masayuki Uda; Yukio Tomioka; Chikara Kouno, all of Tokyo; Hiroshi Ishida; Yukio Yamauchi, both of Kanagawa, all of Japan

[73] Assignee: Rikagaku Kenkyujyo, Tokyo, Japan

[21] Appl. No.: 68,184

[22] Filed: Jun. 30, 1987

[51] Int. Cl.⁴ .............................................. G01F 23/00
[52] U.S. Cl. .................................. 250/372; 250/358.1
[58] Field of Search ................... 250/336.1, 310, 358.1, 250/372, 492.1, 492.2

[56] References Cited

U.S. PATENT DOCUMENTS

| | | | |
|---|---|---|---|
| 4,590,376 | 5/1986 | Smith | 250/358.1 |
| 4,640,626 | 2/1987 | Schmid et al. | 250/310 X |
| 4,652,757 | 3/1987 | Carver | 250/358.1 X |
| 4,670,710 | 6/1987 | Beha et al. | 250/310 X |
| 4,721,910 | 1/1988 | Bokor et al. | 250/310 X |
| 4,740,730 | 4/1988 | Uda et al. | 315/84.51 |

FOREIGN PATENT DOCUMENTS 60-262005 12/1985 Japan.
61-164177 7/1986 Japan.
61-239184 10/1986 Japan.
61-239185 10/1986 Japan.

Primary Examiner—Eugene R. LaRoche
Assistant Examiner—David Mis
Attorney, Agent, or Firm—Wenderoth, Lind & Ponack

[57] ABSTRACT

A photoelectron counter in an open detection chamber in which photoelectrons emitted from a solid surface by a photon irradiation energy are counted, is arranged so as to suppress background noise which produces a false count rate due to photoelectrons which are emitted from solid surfaces outside the subject when scattered rays have reached and irradiated the same surface. The counter uses one or more of options including a film or coating formed with a thickness which is less than several $\mu m$ thickness on parts which are subject to scattered rays incident from the subject, a ray screen for interrupting scattered rays from entering into the detection chamber and/or a center guard provided at the front part of the detector to enable nearby measurement and while interrupting scattered rays.

12 Claims, 5 Drawing Sheets

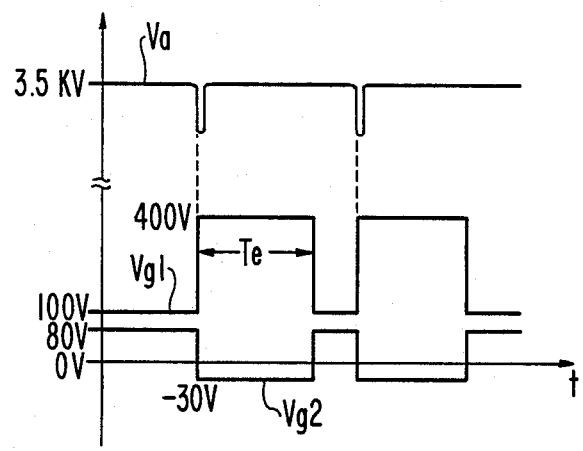
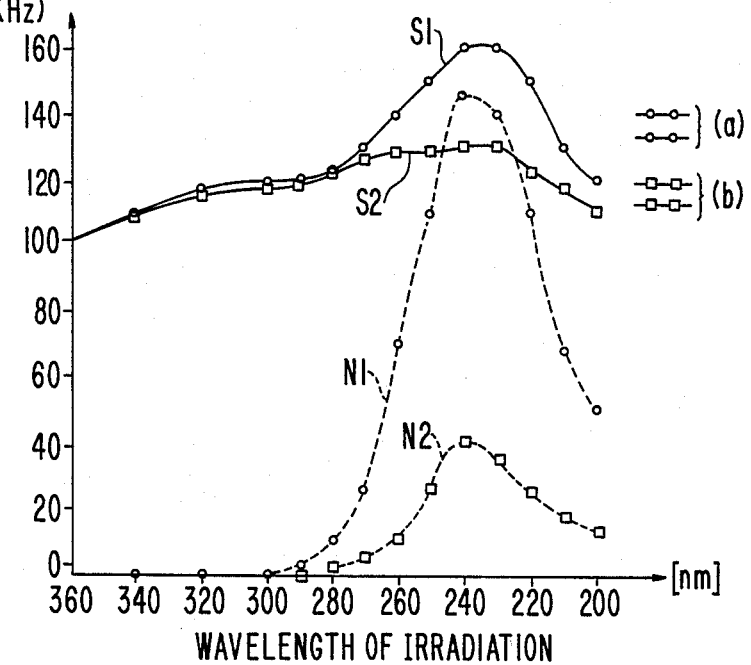
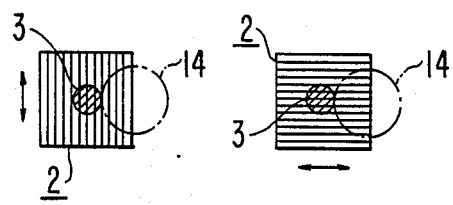

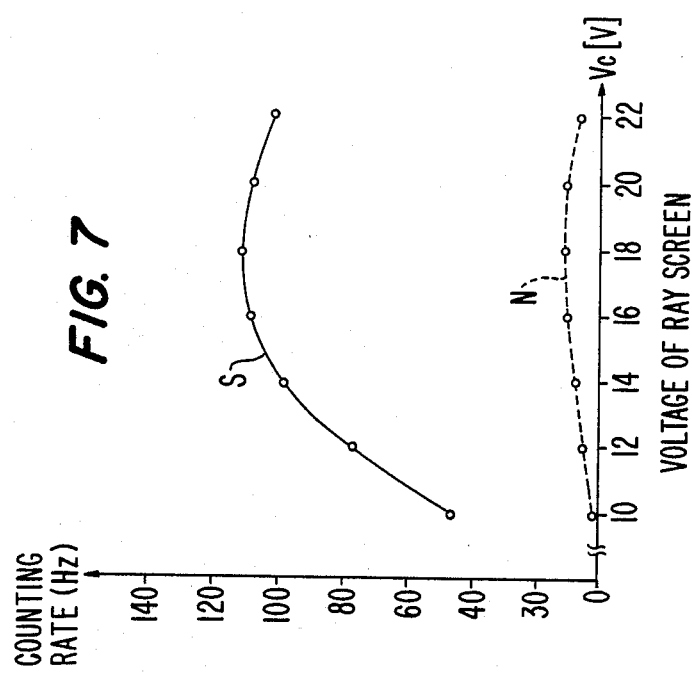
FIG. 7
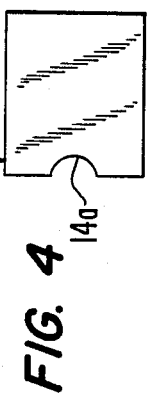
FIG. 4
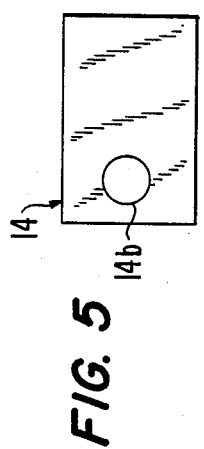
FIG. 5
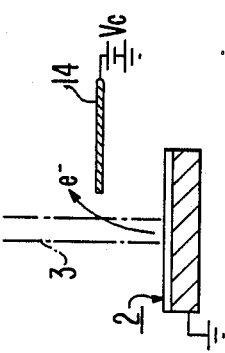
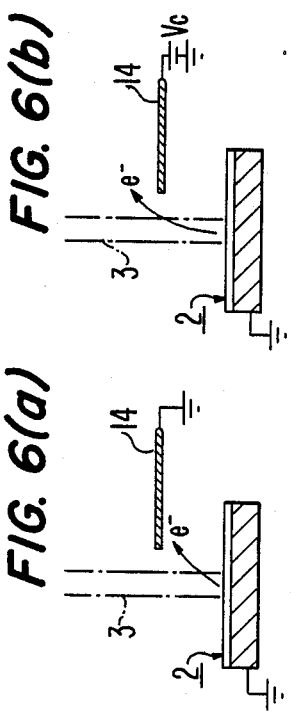
FIG. 6(a)    FIG. 6(b)

OPEN COUNTER FOR LOW ENERGY ELECTRON DETECTION WITH SUPPRESSED BACKGROUND NOISE

BACKGROUND OF THE INVENTION (1) Field of the Invention

This invention relates to a device for detecting photoelectrons in air which will be emitted from solid surfaces by a work function of photon irradiation energy using different photoelectric work functions of respective solids in place of using function of kinetic energy, especially to a device for suppressing background noise as adds false counting rate to true counting rate measured on a detection sample, which will be produced when photoelectrons are emitted by scattered reflection from the detection sample.

(2) Description of the Prior Art

An open counter for photoelectron detection was disclosed in Japanese Patent Open Publication No. 60-262005 (application No. 59-118,818 filed 1984), in contrast with photo electron detection in an ultra-high vacuum. Such a counter was also disclosed by the inventor in the paper, Japanese Journal of Applied Physics Vol. 24 (1985), Supplement 24-4. pp. 284–288.

The photoelectron detection chamber 1 of the device partially shown in FIG. 1A comprises a grid G6 for quenching gas discharge, a grid G7 for suppressing and neutralizing positive ions and an anode A5 using a loop-shaped tungsten filament, wherein the grid G6, G7 and anode A5 are respectively supplied with +100 V, +80 V and +3.5 kV with respect to the chamber 1 grounded as a cathode. The electrons were emitted from the subject upon irradiation by photons and accelerated by two grids to become attached to air or $O_2$ molecules to form negative ions in the atmosphere of the detection chamber. Near the anode A5 electrons were detached from negative ions and caused a gas discharge which was induced by high positive electric fields applied to the anode (+3.5 kV). By detecting a reduction in the high voltage on the anode due to an initial discharge, quenching was carried out by supplying a positive square pulse (+300 V in amplitude and of about 3 msec in width Te) to the quenching grid G6. Some of the positive ions produced around the anode could pass through the quenching grid G6 during a discharge followed by quenching. To neutralize these positive ions, −30 V was supplied to the suppressor grid G7. Such a series of procedures prevented successive and continuous discharges, and enabled electrons in an atmosphere to be counted without either self-quenching or internal quenching. After positive ions were neutralized, the grids G6 and G7 are turned to the initial voltages referred to FIG. 1B.

Secondary discharge incurred by positive ions was avoided by repeating the above procedure for stably counting the rate of photoelectrons in air.

When a ray source spectroscope in FIG. 1A which can change the wave-length of supplied irradiation energy from a lower value (longer wavelength) to a higher value, a certain amount of energy causes photoelectron emission due to the photoelectric effect. The counting rate (Hz) of photoelectrons per second and ray irradiation energy (hv) have the following relationship:

(Hz)$^n \alpha h\nu$, wherein $n = 0.4 \sim 1$ usually, $n = \frac{1}{2}$ for metal.

Photoelectron emission energy is given by a work function and the value of the work function is different for different kinds of substances. In the case of an oxide layer on silicon, the work function of the oxide is larger than that of silicon so that presence of the oxide layer reduces the amount of photoelectrons emitted from that emitted from silicon. When the photoelectrons are given an irradiation energy which is larger than the work function of silicon, the counting rate of photoelectrons N is given as follows:

$\log N = N_0 - T/2.3\lambda$, wherein T is the thickness of the layer: $N_0$ is the counting rate at a thickness of zero: $\lambda$ is the mean free path in the oxide layer. Generally, other substances have equations similar to this. A value of N of $350 \sim 1$ Hz was confirmed in response to thicknesses from $0 \sim 140$ A°. In the above noted paper, compensation was also disclosed for atmospheric pressure, temperature and humidity changes. However, there is no suggestion in the abovenoted paper as to the problem of scattered ray irradiation causing a false increase in the photoelectron counting rate as background noise. It is impossible to obtain an exact counting rate of photoelectrons using suitable compensation equations unless the background noise of scattered ray irradiation was suppressed.

SUMMARY OF THE INVENTION

An object of the present invention is to provide a device for counting photoelectrons in air with a suppressed background noise, which is used to obtain solid surface information regarding friction, abrasion, mechanical deformation, oxidation, catalytic reactions, radiation damage, contamination, thickness of oxidation and work functions, while photoelectrons emitted from peripheral solid surfaces by scattered ray irradiation from the subject cause an erroneous counting rate increase as background noise.

Another object of the present invention is to provide an open counter for low energy electron detection using a ray screen for suppressing emission of extraneous photoelectrons so as to reduce the background noise which cause the false counts to Another object of the present invention is to provide an open device for counting photoelectrons from the subject using a thin layer formed on grids and/or parts with a thickness of less than several $\mu$m so as to thereby to suppress the background noise.

Still another object of the present invention is to provide a device for counting low energy electrons in air using a center guard structure to enable nearby measurement and background noise suppression against the subject.

Background noise may occur so much as to make it impossible to make an exact count of photoelectrons even if a compensation factor was calculated. Referring to FIG. 1A, when a surface of a specimen 2 is not mirror-polished, a ultra-violet beam 3 is radiated to and scattered from the subject surface, so that the scattered rays 10 enter from the low energy electron entrance gate 9 to the inside space. The scattered rays which irradiate inside parts, especially the grids G6 and G7 cause them to emit low energy electrons.

FIG. 2 shows graph of background noise of which the counting rate (Hz) of photoelectrons was plotted against the wavelength of irradiating rays when the open counter was receiving rays scattered from the subject, and the subject was an A1 plate. Curves S1 and S2 are respectively the total counting rate (Hz) of emitted photoelectrons, with S1 be obtained from a specimen polished in the manner illustrated in FIG. 3 (a) and S2 obtained from another specimen as illustrated in FIG. 3(b).

Curves N1 and N2 are respectively the counting rate (Hz) of emitted photoelectrons when the grid G7 was charged to −30 V so as to thereby block incoming low energy electrons from the speciman 2. Detected electrons were emitted from the grids G6 and G7 by irradiation of rays scattered from the specimen 2. Moreover, such background noise counting rates N1 and N2 have peak values near the wavelength 240 nm, respectively. N1 and N2 are respectively observed from the same specimen of FIGS. 3(a) or 3(b) as rated above for S1 or S2. The exact counting rate of low energy electrons which are emitted from the subject will be obtained by the calculation of (S1−N1) or (S2−N2); however, it is impossible to correct the total counting rate (Hz) if the background noise were large. It is still unknown whether an increase in photoelectrons depends on the difference of scattered rays or the thickness changes of the oxide layer as long as the background noise existed. The anode A5 is supplied with a voltage Va by a high voltage source 16; the grid G6 is supplied with a voltage Vg1 by a first pulse generator 18; the grid G7 is supplied with a voltage Vg2 by a second pulse generator 19; the ray screen 14 is supplied with a voltage Vc by a ray screen voltage source 15; and a reduced voltage lower than Va is input to a counting circuit 20 through an amplifier 17 and is corrected by a compensation circuit 21 using a computer to supply the counting rate (Hz) to a display 22.

BRIEF DESCRIPTION OF THE DRAWINGS

FIG. 1B is an electric signal chart for obtaining counting rate (Hz) of photoelectrons by controlling the counter operation;

FIG. 2 is a graph of background noise;

FIG. 3 (a) and FIG. 3 (b) are sample specimens which were polished vertically or transversely for changing the direction of scattering rays;

FIGS. 4 and 5 are respectively a ray screen in plane view;

FIG. 6 (a) and FIG. 6 (b) are illustrations for explaining the potential effect on the charged ray screen;

FIG. 7 is a graph of the relationship between the total counting rate (Hz) and background noise in the open counter along with changes in the voltage supplied to the ray screen;

FIG. 10 is the device in sectional view which is improved by the use of a center guard structure further to enable nearby detection; and FIG. 11 is another example of the center guard structure in sectional view.

DETAILED DESCRIPTION OF THE PREFERRED EMBODIMENT

Figure 1A:
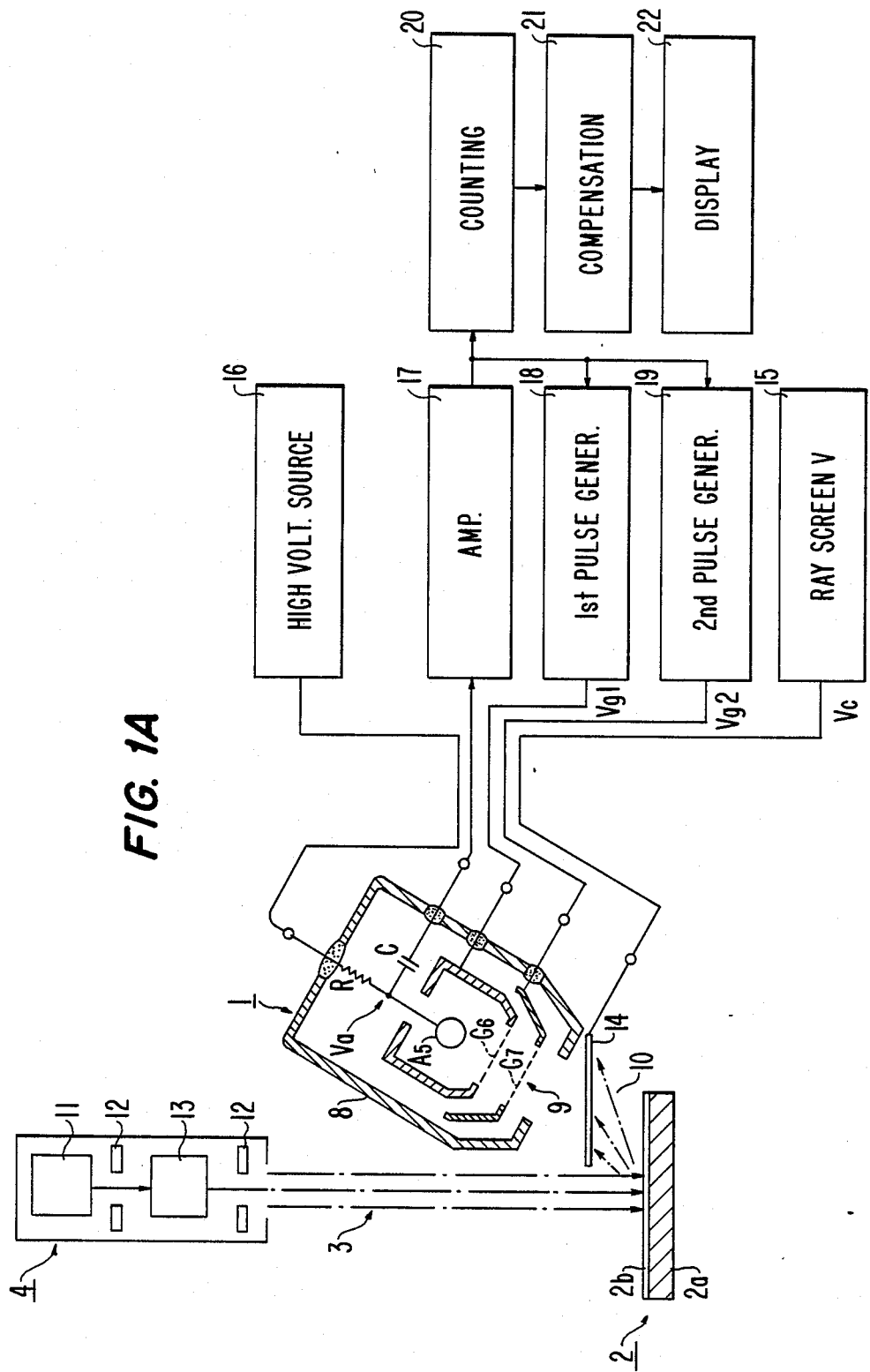
FIG. 1A is a known open counter for low energy electron detection in sectional view together with a ray source device and an operation electric circuit, to which a ray screen 14 is applied according to the present invention.

In FIG. 1A, a ray source unit 4 uses a heavy hydrogen lamp 11, a slit 12 and a spectroscope 13 in which rays of the source 11 pass through the slit 12, and are then dispersed by the spectroscope 13 in to ultraviolet rays of a predetermined wavelength which are irradiated on the surface of the subject 2 as an ultraviolet beam 3 through the slit 12.

Setting the subject 2 on which the ultraviolet beam 3 irradiates in a vertical direction from the ray source unit 4, the photoelectron detector 1 is placed so as to have its electron entrance gate 9 directed obliquely face to face with the surface of the subject 2 on which the beam irradiates. The ray screen 14 which is attached at the detector 1 to cross between the subject 2 and the detector 1 shelters the detector from scattered rays 10, so that the inner part of the electron detector 1 is not irradiated by the scattered rays from the subject 2 through the electron entrance gate 9.

The ray screen 14 uses, for example a plate having a portion 14a cut off like semi-circle through which the ultraviolet beam passes (see FIG. 4), or a plate having a cut off hole 14b for passing the beam therethrough (see FIG. 5). It also uses a plate having no portion cut off like 14a or 14b to pass the beam but interrupt the scattering rays.

To the ray screen 14, a DC voltage Vc is supplied from an electric source 15. The charged ray screen 14 makes emitted low-energy electrons or anions drift forward to the anode A5 which is charged to 3.5 KV, preventing them from being repelled outside. The potential which is supplied to a specimen will be controlled to be a voltage equal to the voltage Vc of the ray screen voltage source 15, so that the electric field thus produced at the ray screen 14 makes so as to cause low energy electrons emitted from the specimen 2 to drift to the anode A5 by overriding the ray screen. If the electric potential of the ray screen 14 is equal to that of the subject 2 which is grounded as shown in FIG. 6(a), photoelectrons or anions with low energy, which were emitted from the surface of the subject 2 upon irradiation of the ultraviolet beam 3 or made accompanyingly by the emitted photoelectrons, are being induced forward to the photoelectron open-counter 1 as is, but obstacled by the ray screen 14 so as not to drift towards the anode A5. Thus, the exact counting rate (Hz) was not always measured.

Referring to FIG. 6(b), the subject 2 is grounded and the ray screen 14 is supplied with the Vc voltage inasmuch as remarkable effect will be confirmed in FIG. 7 illustrating the relationship between the total counting rate S (Hz) and the background noise N (Hz) corresponding to the change of the Vc voltage applied to the ray screen 14.

In the graph, the total counting rate S was measured at 3.94 KV of the anode A5 (Va), 100 V of the first grid G6 (Vg1) and 80 V of the second grid G7 (Vg2) regarding an A1 plate as the subject 2, and background noise N (Hz) was measured at −30 V of the second grid G7 (Vg2).

Analyzing the curve S increasing with higher voltage Vc and the saturated curve between 16–20 V, it confirmed that the roundabout way of low-energy electrons or anions could be made from the subject 2 to the anode A5 through the photoelectron entrance gate 9 in spite of the presence of the ray screen 14. Meanwhile, the background noise N which was measured at −30 V of the second grid G7 (Vg2) was suppressed under 10 cps independent from potential of the ray screen 14. The Vc voltage to the ray screen 14 is preferably selected from a range 16-20 V if the subject is grounded. Under 10 V, emitted photoelectrons or anions would be obstacled to drift towards the anode A5 by the low potential of the ray screen 14.

Background noise is further suppressed by use of surface layer application on grids G6 and G7 which are positioned behind the photoelectron entrance gate 9, and the surface layer is to have a work function larger than that for emitting photoelectrons by irradiation of the scattered rays from the subject, such that photoelectron emission can be prevented from the surface layer applied on grids having a larger work function. Emission may be prevented by insuring that the layer thickness is larger than a range of from 30 to 400 A° for a large work function. This was verified by the fact that the mean free path of low-energy electrons with energies less than 10 eV is on the order of a few micrometers. From the surface of metal making grids G6 and G7, photoelectron emission will be efficiently prevented because the surface layer has a work function larger than that of the grid metal.

Figure 9:
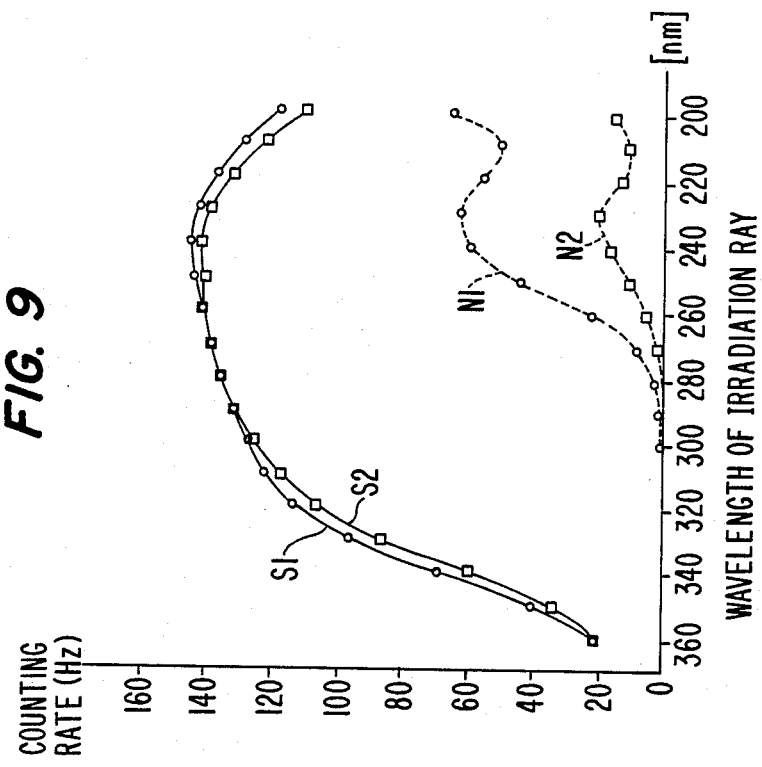
FIG. 9 is a graph of the counting rate (Hz) and background noise in the open counting device improved by the use of a chrome oxide layer structure on the surface of grids.
Figure 8:
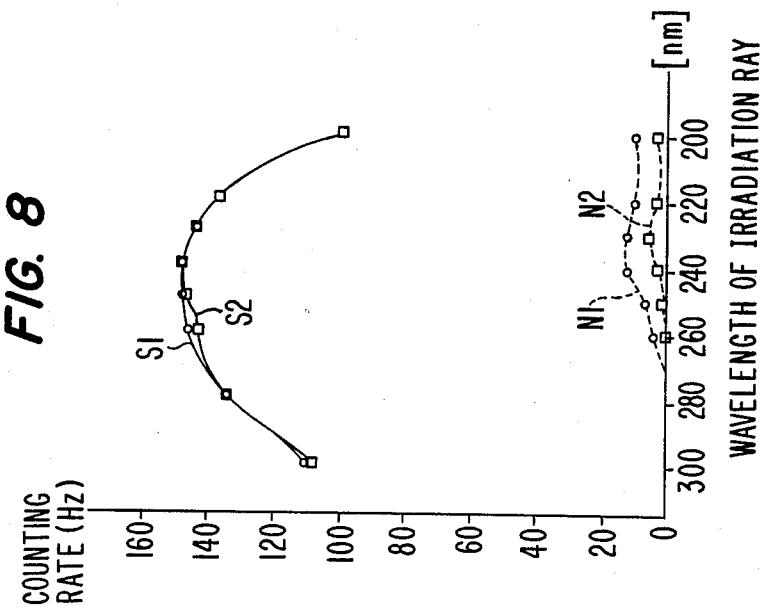
FIG. 8 is a graph of the counting rate (Hz) and background noise in the open counter improved by the use of the ray screen structure.

Since grids G6 and G7 act to induce photoelectrons or anions towards the anode A5 in the electric field, the thickness of the surface layer will be restricted to be able to keep the same function, because the function of an efficient electric field is likely lost with a greater layer thickness. A thicker applied layer tends to make the electric field weak. The thickness should therefore be less than a few μm to prevent photoelectrons from being emitted from the grid metal by irradiation of scattered rays. A graph of FIG. 9 shows that the suppression effect against background noise is less than ½ in comparison with FIG. 2 having no layer application thereon. Accordingly, the S/N ratio may be positively improved so that exact counting rate (Hz) will be more reliably measured out. Curves S1 and N1 are from the specimen 2 of FIG. 3(a), and S2 and N2 are from FIG. 3(b). Chrome oxide was used to make the layer or film, and it is useful to oxidize the surface of a stainless grid. Furthermore, a layer or film of Nitride, or coating of an organic compound or the like causes the same suppression function on the surface of grid. When the surface layer formation is designed to have a thickness of less than 1 μm, the dielectric affect will be easily controlled so as not to make total design complicated.

FIGS. 10 and 11 illustrate two examples of a center guard structure for suppressing the background noise of scattered ray irradiation. A forward end of optical fiber 101a into which an irradiation ray is supplied from the ray source 4 faces to the subject 2 passing through the photoelectron entrance gate 9 of the open counter 1, which is guided within a tubelike isolated holder 102 extending from the top to the outside of the gate 9 of the open counter case 8. A level ring anode A5 is horizontally supported by a conductor A6 around the isolated holder 102, and the forward end 102a of the isolated holder is extended over the gate 9 towards the subject 2 which is positioned at a predetermined distance from a focussing lens 103 of the optical fiber 101. An irradiation spot on the surface of the subject 2 may be controlled within a circle which is more or less than a μm order diameter.

Between the open end of the gate 9 and the peripheral edge of the holder 102, the ray obstacle angle θ is defined by arrow A to repel the entrance of scattering rays from the subject 2, so that the forward end 102a acts as a center guard structure. A contact tool 102b limits the upper measuring position secures nearby measurement for checking the thickness of the oxidized pattern layer on a VLSI chip on which the irradiation spot shall be focussed at a circle of a submicron order diameter.

In FIG. 11, the center guard structure 102' is provided with a horn head as another example, in which a magnifying lens 103a is set at the forward end of the optical fiber 101 for forming an irradiation spot larger than the optical fiber diameter. The ray obstacle angle θ is established between the horn head edge and the open end of the gate 9. This structure is useful for forming a controlled and larger spot, for example, when a disfigurement such as scratches, abrasion or the like on the surface of solids will be turned to surface information by continually irradiating the optical fiber ray beam on a predetermined area at an accurately controlled and magnified spot over the surface of subject 2 by a nearby measurement. In place of the horn head shape, a disk shape or an umbrella shape member are provided with the center guard structure for respective needs.

The center guard structure 102 may be modified by replacing the forward end by a metal or conductive tube to which the Vc is supplied. It is most preferable to combine effects of the ray screen, the surface layer or film application and the center guard structure to effectively supress the background noise of scattered rays.

What is claimed is:

1. A device for counting photoelectrons in a photolectron detector, which are emitted from a subject in response to irradiation by ray irradiation, in which the open photoelectron detector consists of photoelectron emission prohibition means for preventing photoelectrons from being emitted from inner surfaces of the detector due to rays scattered from the same subject; wherein said photoelectron emission prohibition means consists of a surface layer or film having a work function which is greater than that of parts of the detector, and which is applied to the parts from which photoelectrons are emitted due to rays scattered from the subject.

2. A device according to claim 1, wherein the photoelectron detector is arranged independent from an irradiation ray source which outputs an irradiation ray which is led through an optical fiber to a point for making a spot over the surface of the subject to limit a scattering range on which the irradiation ray is scattered from the subject.

3. A device according to claim 1, in which an optical device is provided with an optical fiber having a forward end for forming an irradiation spot corresponding to measurements of the subject and for limiting the scattering range.

4. A device according to claim 2, in which an optical device is provided with an optical fiber having a forward end for forming an irradiation spot corresponding to measurements of the subject and for limiting the scattering range.

5. A device for counting photoelectrons in a photolectron detector, which are emitted from a subject in response to irradiation by ray irradiation, in which the open photoelectron detector consists of photoelectron emission prohibition means for preventing photoelectrons from being emitted from inner surfaces of the detector due to rays scattered from the same subject; wherein said photoelectron emission prohibition means consists of a ray screen for preventing scattered rays from being radiated to the detector from the subject, to which is supplied a voltage to produce an electric field for deflecting away from the detector the subject emission photoelectrons or anions formed with the same emitted photoelectrons towards the detector.

6. A device according to claim 5, wherein the photoelectron detector is arranged independent from an irradiation ray source which outputs an irradiation ray which is led through an optical fiber to a point for making a spot over the surface of the subject to limit a scattering range on which the irradiation ray is scattered from the subject.

7. A device according to claim 5, in which an optical device is porovided with an optical fiber having a forward end for forming an irradiation spot corresponding to measurements of the subject and for limiting the scattering range.

8. A device according to claim 6, in which an optical device is provided with an optical fiber having a forward end for forming an irradiation spot corresponding to measurements of the subject and for limiting the scattering range.

9. A device for counting photoelectrons in a photoelectron detector, which are emitted from a subject in response to irradiation by ray irradiation, in which the open photoelectron detector consists of photoelectron emission prohibition means for preventing photoelectrons from being emitted from inner surfaces of the detector due to rays scattered from the same subject; wherein said photoelectron emission prohibition means consists of a ray screen for preventing scattered rays from being radiated to the detector from the subject, said ray screen being formed with a large work function layer or film on a surface of the screen which would emit photoelectrons when irradiated with the scattered rays from the subject.

10. A device according to claim 9, wherein the photoelectron detector is arranged independent from an irradiation ray source which outputs an irradiation ray which is led through an optical fiber to a point for making a spot over the surface of the subject to limit a scattering range on which the irradiation ray is scattered from the subject.

11. A device according to claim 9, in which an optical device is provided with an optical fiber having a forward end for forming an irradiation spot corresponding to measurements of the subject and for limiting the scattering range.

12. A device according to claim 10, in which an optical device is provided with an optical fiber having a forward end for forming an irradiation spot corresponding to measurements of the subject and for limiting the scattering range.

* * * * *